United States Patent [19]

Ueda

[11] Patent Number: 4,832,473
[45] Date of Patent: May 23, 1989

[54] ENDOSCOPE WITH ELASTIC ACTUATOR COMPRISING A SYNTHETIC RUBBER TUBE WITH ONLY RADIAL EXPANSION CONTROLLED BY A MESH-LIKE TUBE

[75] Inventor: Yasuhiro Ueda, Tokyo, Japan

[73] Assignee: Olympus Optical Co., Ltd., Tokyo, Japan

[21] Appl. No.: 151,322

[22] Filed: Feb. 1, 1988

[30] Foreign Application Priority Data

| Feb. 6, 1987 | [JP] | Japan | 62-25944 |
| Oct. 8, 1987 | [JP] | Japan | 62-252398 |
| Oct. 8, 1987 | [JP] | Japan | 62-252399 |
| Oct. 8, 1987 | [JP] | Japan | 62-252400 |

[51] Int. Cl.$^4$ .......................... A61B 1/06; G02B 6/06; G02B 7/04; G02B 7/22
[52] U.S. Cl. ................................... 350/506; 350/577; 350/632; 350/563; 350/96.26; 128/6
[58] Field of Search ............... 350/506, 577, 632, 563, 350/573, 96.26; 128/6

[56] References Cited

U.S. PATENT DOCUMENTS

| 3,572,325 | 3/1971 | Buzell et al. | 128/6 |
| 3,739,770 | 6/1973 | Mori | 128/6 |
| 3,799,151 | 3/1974 | Fukaumi et al. | 128/6 |
| 4,290,421 | 9/1981 | Siegmund | 128/6 |
| 4,292,961 | 10/1981 | Kawashima | 128/6 |
| 4,575,185 | 3/1986 | Wentzell et al. | 350/96.26 |
| 4,620,769 | 11/1986 | Tsuno | 350/96.26 |

FOREIGN PATENT DOCUMENTS

| 179905 | 10/1954 | Austria | 350/96.26 |
| 59-146636 | 8/1984 | Japan . | |

Primary Examiner—Jon W. Henry
Attorney, Agent, or Firm—Ladas & Parry

[57] ABSTRACT

An endoscope has a flexible insertion portion having distal and proximal end portions. Elastic actuators for bending the insertion section are mounted in the insertion section. Each elastic actuator has an inner space and is longitudinally expanded/contracted when a fluid is supplied to/discharged from the inner space. A converting unit is provided in the insertion section and converts an expanding/contracting motion of the elastic actuator into a bending motion of the insertion section. The elastic actuator is connected to a control unit for controlling the fluid in the inner space of the elastic actuator.

19 Claims, 16 Drawing Sheets

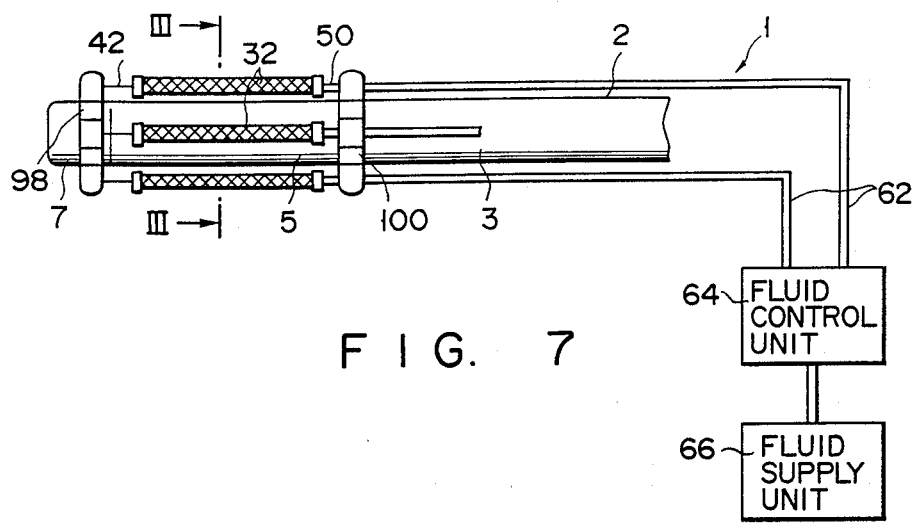
F I G. 7
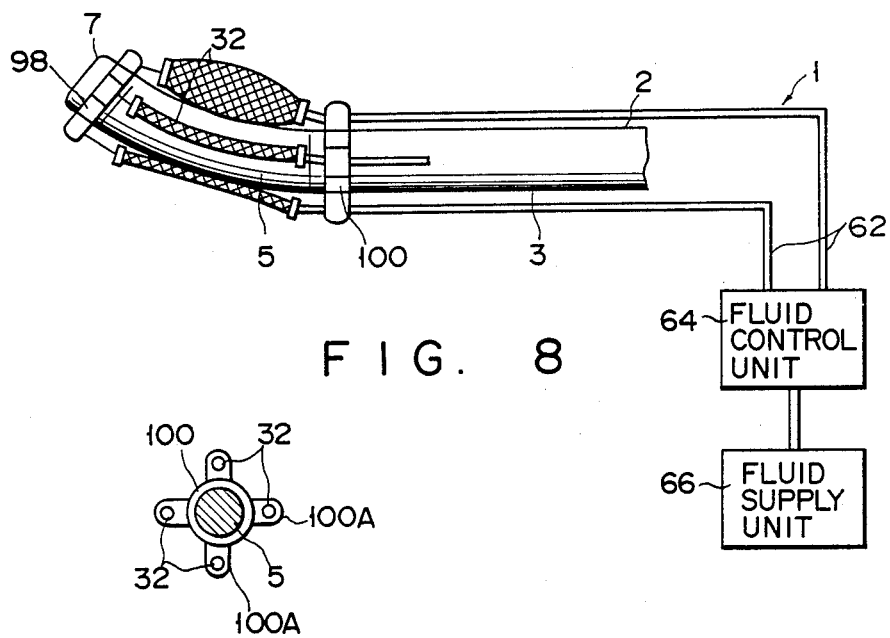
F I G. 8
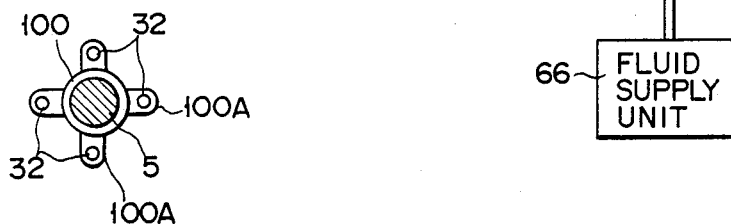
F I G. 9

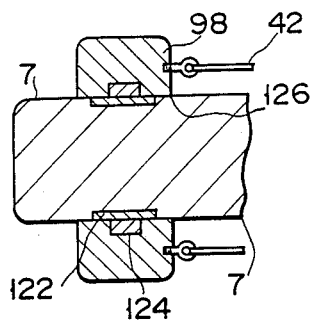
F I G. 13
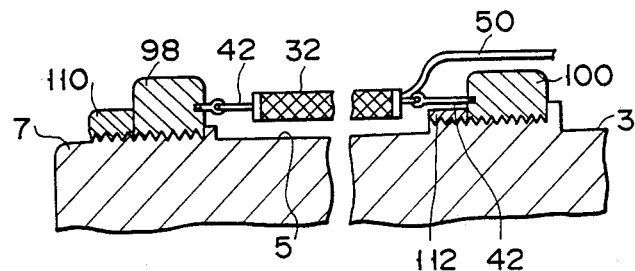
F I G. 14
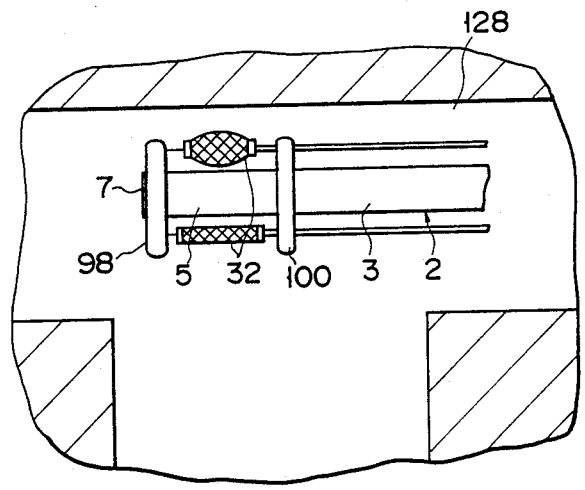
F I G. 15

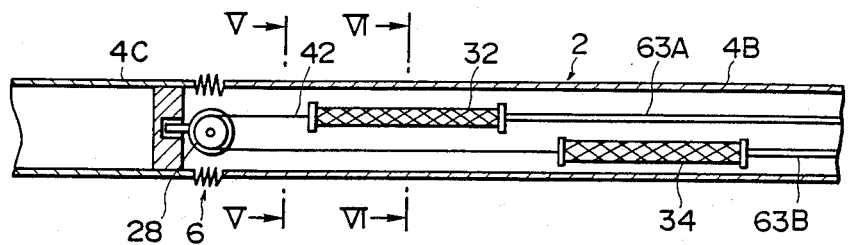
FIG. 26
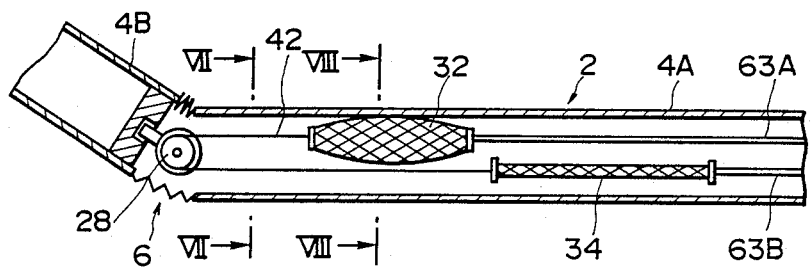
FIG. 27
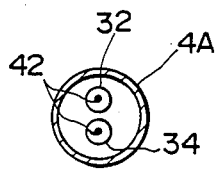 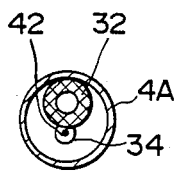 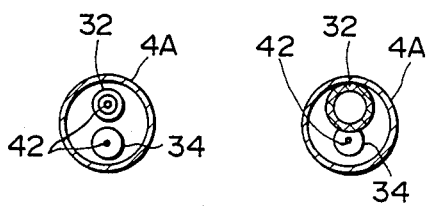
FIG. 28  FIG. 30
FIG. 29  FIG. 31

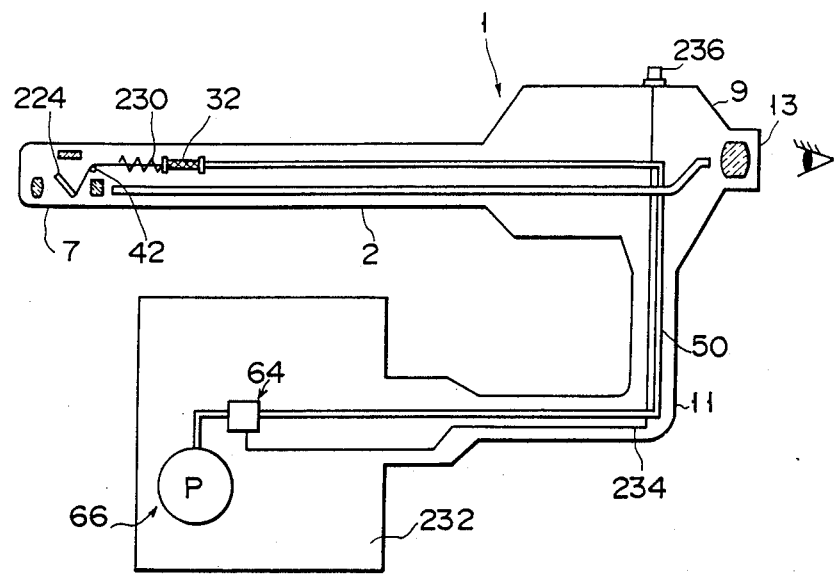
F I G. 32
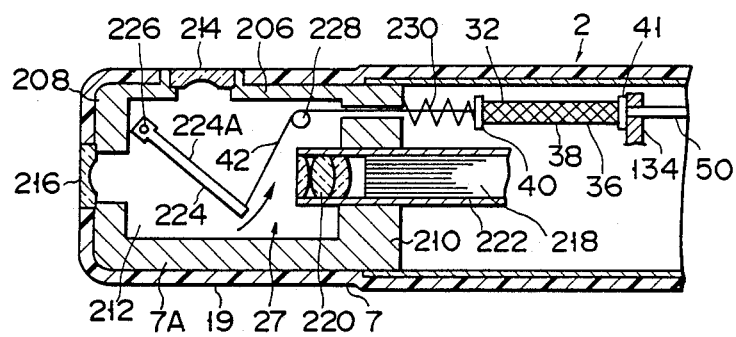
F I G. 33

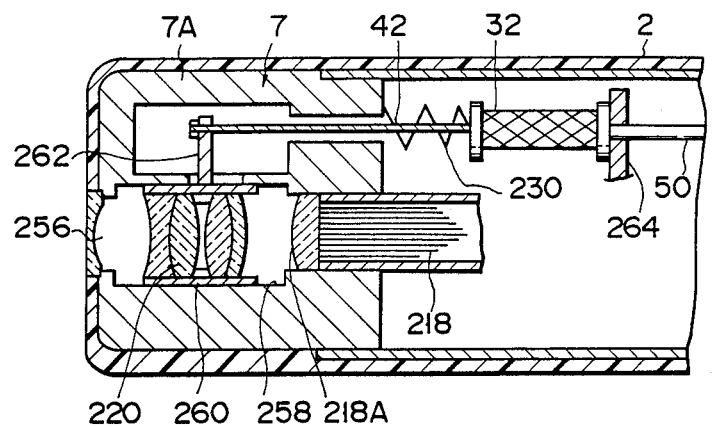
F I G. 37
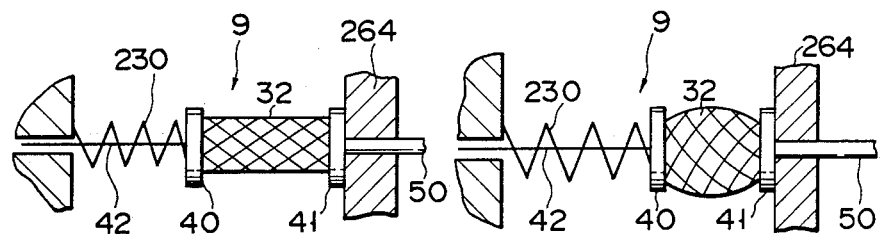
F I G. 38     F I G. 39

ENDOSCOPE WITH ELASTIC ACTUATOR COMPRISING A SYNTHETIC RUBBER TUBE WITH ONLY RADIAL EXPANSION CONTROLLED BY A MESH-LIKE TUBE

BACKGROUND OF THE INVENTION

A. Field of the Invention

The present invention relates to an endoscope having an elastic actuator driven by supplying or discharging a fluid.

B. Description of the Prior Art

A typical industrial endoscope is used to check an internal portion which cannot be directly viewed from the outside by an operator, e.g., an engine of an aircraft or an interior of a narrow tube. Such an industrial endoscope has illumination and observation optical systems at its distal end portion of an insertion portion. Therefore, even if a portion to be observed is located at a deep position of a bent path, the distal end portion can be guided to a position close to the portion to be observed.

Japanese Patent Disclosure (Kokai) No. 59-146636 discloses a typical industrial endoscope. This endoscope has an insertion portion incorporating illumination and observation optical fiber bundles and a distal end constitution portion mounted at the distal end of the insertion portion. A cylinder and a piston are provided in the insertion portion and move relative to each other by a pressure of a fluid supplied from the outside. A joint member of the insertion portion is bent by a relative motion of the cylinder and the piston, thereby bending the insertion portion.

Japanese Patent Disclosure (Kokai) No. 61-122834 discloses a typical endoscope to be inserted into a human body to observe a diseased part or the like. An insertion portion of this endoscope incorporates illumination and observation optical fiber bundles and a plurality of operation wires. One end of each operation wire is connected to a distal end constitution portion, and the other end thereof is connected to an angle knob provided to an operation portion. By pushing/pulling the operation wires by the angle knob, a bending portion of the insertion portion can be bent.

However, an endoscope having a cylinder and a piston driven by a pressure of a fluid in its insertion portion has a complicated arrangement and a heavy weight and requires a high fluid pressure to drive the piston inside the cylinder. In addition, since a drive unit of the insertion portion does not have elasticity, the insertion portion may cause damage to a peripheral unit when it is brought into contact with the unit.

In an endoscope in which an insertion portion is relatively long and angle operation wires are incorporated in the insertion portion, friction between the angle operation wires and wire guides is increased. Therefore, a large power is required to operate an angle knob.

Another typical example of an endoscope is an endoscope having an observation optical system, in which an observation field of the endoscope is changed or focus adjustment of the observation optical system is performed by operating operation wires inserted in a flexible tube portion and a bending tube portion of an insertion portion. However, in this endoscope, since a large space for housing the operation wires so that they can move forward and backward must be formed in the insertion portion, an outer diameter of the insertion portion is increased. In addition, friction between the operation wires and wire guides prevents a correct operation, and expansion of the operation wires degrades accuracy of focus adjustment.

SUMMARY OF THE INVENTION

It is an object of the present invention to provide an endoscope having a relatively long insertion section and, more particularly, to an endoscope whose insertion section can be easily and accurately bent.

The above object of the present invention can be achieved by the following endoscope. That is, this endoscope has a flexible insertion section having distal and proximal end portions. Elastic actuators for bending the insertion section are mounted in the insertion section. Each of the elastic actuators has an inner space and is longitudinally expanded/contracted when a fluid is supplied to/discharged from the inner space. A converting unit is provided in the insertion section and converts an expanding/contracting motion of the elastic actuator into a bending motion of the insertion section. The elastic actuator is connected to a control unit for controlling a fluid to be supplied to the inner space.

In an endoscope according to the present invention, an insertion section can be bent by an elastic actuator. Therefore, as compared with a typical endoscope and the like in which an insertion section is bent by operating an angle knob, the endoscope of the present invention can be easily and reliably operated by an operator.

BRIEF DESCRIPTION OF THE DRAWINGS

FIGS. 7 and 8 are schematic side views of an insertion portion of an endoscope according to a second embodiment of the present invention;

FIG. 9 is a sectional view taken along line III—III of FIG. 7;

FIG. 13 is a longitudinal sectional view of a second modification of the mounting portion of the elastic actuator;

FIGS. 14 and 15 are side views of a modification of the elastic actuator according to the second embodiment;

FIGS. 26 and 27 are longitudinal sectional views of a modification of the insertion portion of the endoscope according to the third embodiment;

FIG. 28 is a cross-sectional view taken along line V—V of FIG. 26;

FIG. 29 is a cross-sectional view taken along line VI—VI of FIG. 26;

FIG. 30 is a cross-sectional view taken along line VII—VII of FIG. 27;

FIG. 31 is a cross-sectional view taken along line VIII—VIII of FIG. 27;

FIG. 32 is a schematic longitudinal sectional view of an endoscope according to a fourth embodiment of the present invention;

FIG. 33 is a longitudinal sectional view of an insertion portion of the endoscope shown in FIG. 32;

FIG. 37 is a longitudinal sectional view of a modification of the insertion portion of the endoscope according to the fourth embodiment; and FIGS. 38 and 39 are side views of a modification of the elastic actuator according to the fourth embodiment.

DETAILED DESCRIPTION OF THE PREFERRED EMBODIMENTS

A first embodiment of an endoscope according to the present invention will be described below with reference to FIGS. 1 to 5.

Figure 1:
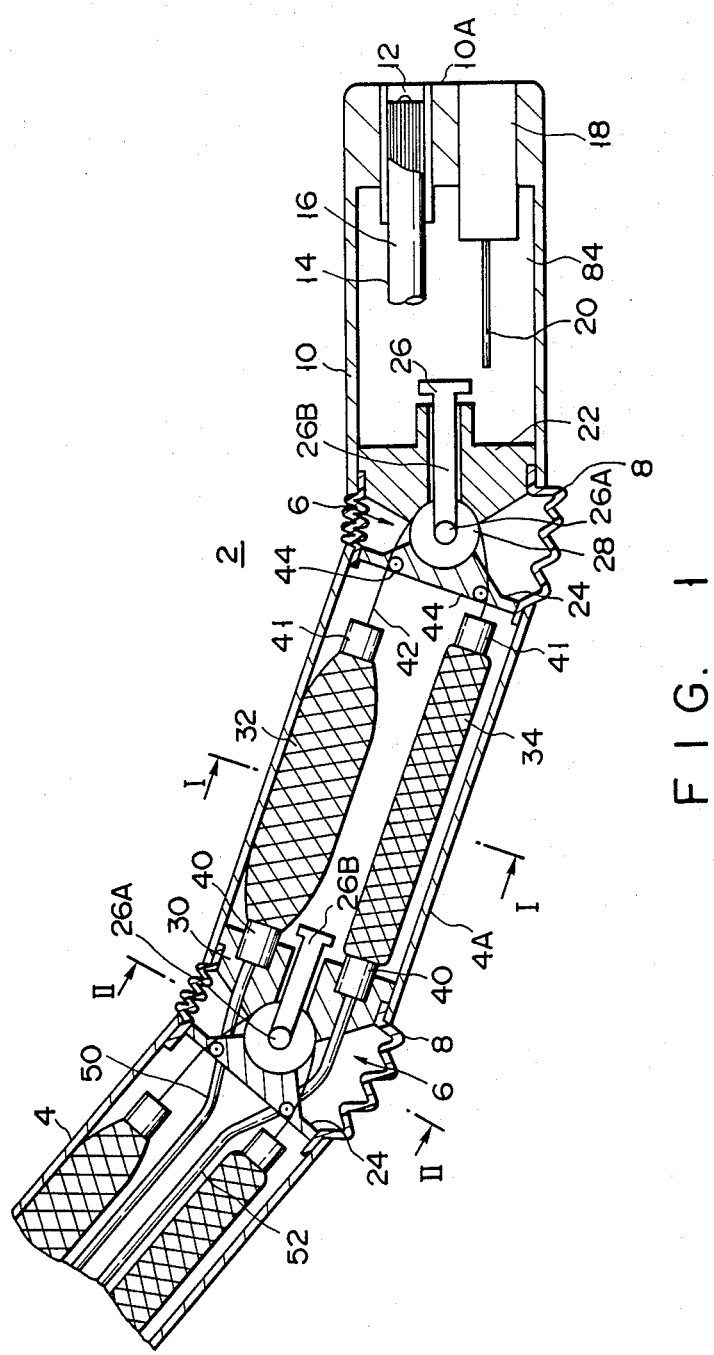
FIG. 1 is a longitudinal sectional view of an insertion portion of an endoscope according to a first embodiment of the present invention.

An endoscope for, e.g., an industrial application shown in FIG. 1 has insertion section 2. In insertion section 2, a large number of segments 4 each having a substantially cylindrical outer shape are sequentially connected with each other through joint portions 6. A portion between segments 4 is air-tightly covered with bellows 8 made of a material having elasticity such as rubber.

Distal end segment 10 is provided at the distal end of insertion section 2. Illumination lens 12 is provided at distal end portion 10A of segment 10, and the distal end of light guide fiber 16 as illumination transmission unit 14 is mounted inside lens 12. TV camera 18 is provided at distal end portion 10A and photographs a portion to be observed which is illuminated with light supplied from fiber 16. Camera cable 20 is connected to camera 18.

Both of cable 20 and fiber 16 extend from distal end portion 10A to the proximal end portion (not shown) of insertion section 2.

As shown in FIG. 1, support member 22 is provided in a rear end portion of distal end segment 10. The rear end of support member 22 and the front end of front support member 24 of second segment 4A are pivotally coupled with each other through shaft member 26 having radially extending shaft portion 26A and axially extending holding portion 26B. First pulley 28 is concentrically provided on shaft portion 26A of shaft member 26 and is fixed to support member 22 by holding portion 26B.

Figure 4:
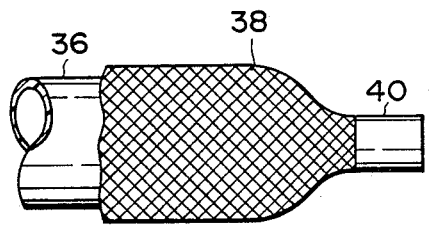
FIG. 4 is a partially cutaway side view of an elastic actuator according to the present invention.

Front support member 24 is mounted on a front end portion of segment 4A, and rear support member 30 is mounted on a rear end portion thereof. One end of each of rubber actuators 32 and 34 as elastic actuators provided symmetrically about the central axis of rear support member 30 is connected to its front portion. Actuators 32 and 34 have the same arrangement and are shown in FIG. 4. That is, as shown in FIG. 4, each actuator has synthetic rubber tube 36 therein. Tube 36 is covered with mesh-like tube 38, and mouthpieces 40 are mounted on both ends of tube 36.

Both end portions of wire 42 are coupled to end portions of actuators 32 and 34, respectively. Wire 42 is wound around second pulley 44 and first pulley 28, and a central portion of wire 42 is coupled to first pulley 28.

Figure 3:
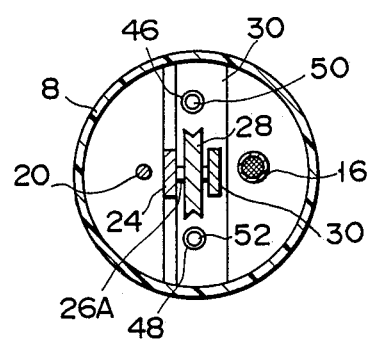
FIG. 3 is a cross-sectional view taken along line II—II of FIG. 1.

As shown in FIG. 3, through holes 46 and 48 are formed in rear support member 30 to extend backward from mounting portions of actuators 32 and 34. Fluid paths 50 and 52 extending from the proximal end portion of insertion section 2 are air-tightly coupled to the other ends of actuators 32 and 34 via holes 46 and 48.

Segments 4 are sequentially connected to the rear portion of second segment 4A in the same manner a that of segment 4A. Rear end portions of paths 50 and 52 provided in a number proportional to that of the segments integrally extend from the proximal end portion of insertion section 2.

Figure 5:
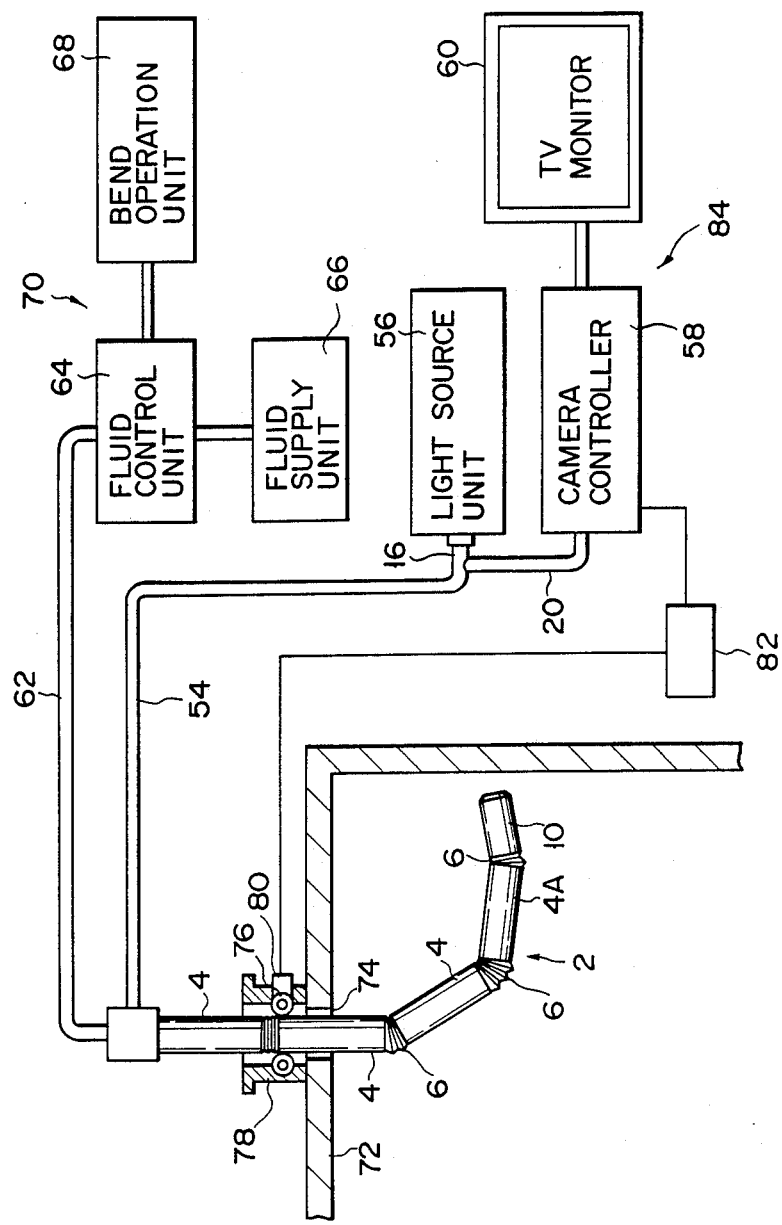
FIG. 5 is a schematic block diagram of an endoscope system according to the present invention.

As shown in FIG. 5, fiber 16 and cable 20 integrally extend as light guide cable 54 from the proximal end portion of insertion section 2. Fiber 16 branched from an intermediate portion of cable 54 is connected to light source unit 56, and cable 20 is connected to camera controller 58. Controller 58 is connected to TV monitor 60.

A plurality of paths 50 and 52 are integrally extend as fluid supply tube 62 from insertion section 2 and connected to fluid control unit 64. Fluid control unit 64 is connected to fluid supply unit 66 and bending operation unit 68. Control means 70 is constituted by units 64, 66, and 68.

An operation of the endoscope according to the first embodiment will be described below.

For example, base 78 having a plurality of rollers 76 is provided to examination hole 74 of tank 72 as an object to be examined. A rotational amount of rollers 76 is detected by potentiometer 80 and detection portion 82, and an insertion length of insertion section 2 of the endoscope is calculated on the basis of a detected value. The calculated insertion length can be displayed at a portion of a screen of monitor 60 through controller 58.

In this endoscope, light is supplied from light source unit 56 to the distal end of insertion section 2 through fiber 16, an object to be observed is photographed by camera 18 under illumination of light. An image signal is displayed as an image on monitor 60 through object image transmission unit 84 consisting of cable 20 and controller 58.

Figure 2:
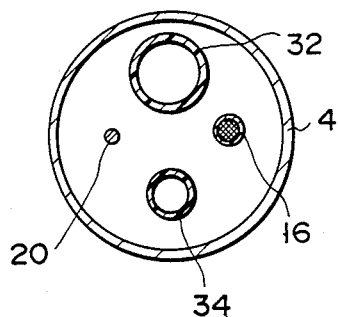
FIG. 2 is a cross-sectional view taken along line I—I of FIG. 1.

A bend instruction input to bend operation unit 68 is converted into a control signal and supplied to fluid control unit 64. As a result, a supply amount of a fluid such as air supplied from fluid supply unit 66 can be adjusted. The adjusted fluid is supplied to actuators 32 and 34 through paths 50 and 52. In this case, fluid control unit 64 supplies the fluid to one of actuators 32 and 34 provided as a pair as shown in FIG. 1. Assuming that the fluid is supplied to actuator 32, the diameter of actuator 32 is increased as shown in FIG. 2, and its length is reduced in accordance with an increase in diameter. Since actuator 32 is covered with mesh-like tube 38, it expands only in the radial direction. Wire 42 is pulled by actuator 32 and at the same time drives first pulley 28. As a result, distal end segment 10 is bent toward actuator 32. In this case, fluid control unit 64 does not supply the fluid to actuator 34, and actuator 34 is expanded in the longitudinal direction. Therefore, an internal pressure is applied on actuator 34 and discharges the fluid therein through path 52.

In order to set distal end segment 10 parallel to second segment 4A, the fluid having the same pressure is supplied to both of actuators 32 and 34 so that both the actuators expand radially to some extent. In order to maximally bend segment 10, the length of one of the actuators is minimized, and that of the other one is maximized.

Other segments 4 can be similarly bent.

In the endoscope according to the present invention, even if insertion section 2 is inserted into, e.g., a tank having a large space, insertion section 2 can hold its own weight. Therefore, a desired portion can be reliably observed. In addition, since a stiffening force for maintaining a shape of insertion section 2 is obtained by a pressure of a fluid such as air, insertion section 2 always has elasticity and hence does not cause damage to another object when it is brought into contact therewith.

The endoscope according to the present invention has a relatively simple arrangement and therefore is light in weight. In addition, since a fluid is used as a drive source, an operation can be safely performed in a combustion gas.

Note that in the first embodiment, the TV camera, camera cable 20, and the like are used as object image transmission unit 84. However, a solid-state image element (CCD), an image guide fiber, or the like may be similarly used. In addition, in the above embodiment, insertion section 2 is bent in two directions. However, by combining segments 4 having different bending directions, insertion section 2 can be bent in four directions.

Furthermore, a chain or the like may be used as wire 42. Although a fluid supplied to actuators 32 and 34 is air in the first embodiment, another fluid may be used. In addition, by connecting a computer to the bend operation unit and storing a predetermined bend pattern in the computer, the insertion portion can repeatedly execute the same operation to uniformly perform examination.

A modification of the elastic actuator according to the first embodiment will be described below with reference to FIG. 6.

Figure 6:
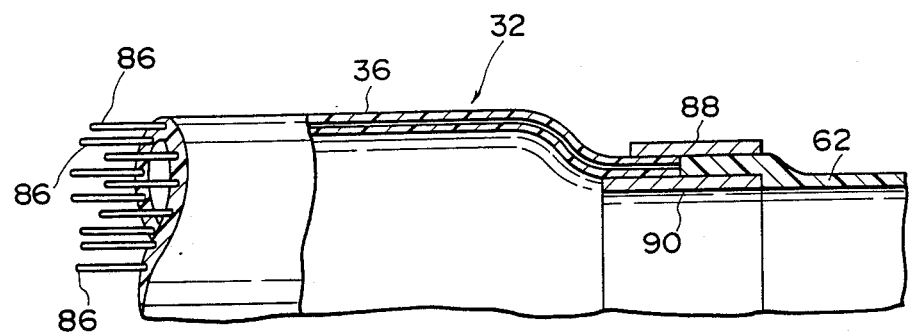
FIG. 6 is a partial sectional view of a modification of an elastic actuator according to the first embodiment.

In actuator 32 shown in FIG. 6, a plurality of wire members 86 such as stainless steel wires or polyester fibers are embedded parallel to each other at predetermined intervals in a wall of tube main body 36 along its longitudinal direction. Both ends of actuator 32 are fastened by first and second metal pieces 88 and 90 from the outside and inside and hence are air-tightly coupled to fluid path 62.

Therefore, a size obtained when the elastic actuator, i.e., actuator 32 is maximally expanded is defined to a predetermined size, and actuator 32 can be easily expanded in the radial direction.

In the endoscope according to the first embodiment, a pair of actuators 32 and 34 are provided as the elastic actuators to bend joint portion 6. However, a single actuator or three or more actuators may be provided.

A second embodiment of the endoscope according to the present invention will be described below with reference to FIGS. 7 to 10.

Main body 1 of an endoscope shown in FIG. 7 has insertion section 2 having flexible portion 3 and bending portion 5. Distal end constitution portion 7 is provided at the distal end of bending portion 5. Insertion section 2 incorporates an image guide, a light guide, and a channel (none of which is shown). A plurality of elastic actuators 32 are provided on an outer circumference of bending portion 5 and bend bending portion 5 so that constitution portion 7 can be moved vertically and in a left-to-right direction.

Actuator 32 and its mounting structure will be described below. Actuator 32 has synthetic rubber tube 36. Tube 36 is covered with mesh-like tube 38, and mouthpieces 40 and 41 are coupled to both ends of tube 36. Air-supply pipe 50 having rigidity such as a synthetic resin pipe is connected to mouthpiece 40 and communicates with the interior of tube 36. Wire 42 is connected to mouthpiece 41.

Figure 10:
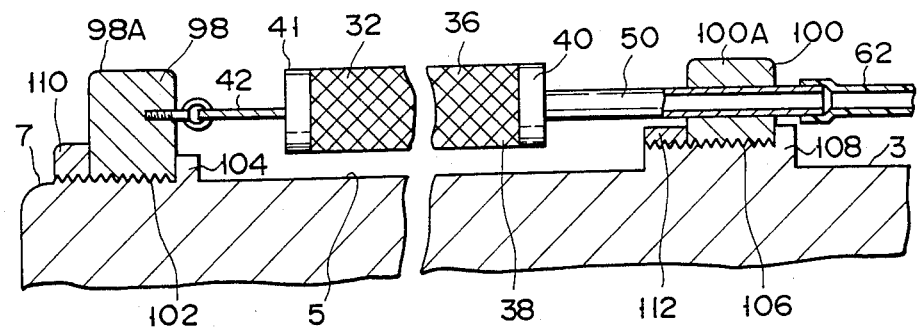
FIG. 10 is a partial sectional view of a peripheral portion of a mounting portion of an elastic actuator according to the second embodiment.

As shown in FIG. 10, first fixing member 98 is fixed to a rear portion of distal end constitution portion 7, and second fixing member 100 is fixed to a front end portion of flexible portion 3. That is, threaded portion 102 and annular stopper 104 are provided on an outer surface of distal end constitution portion 7, and threaded portion 106 and annular stopper 108 having diameters larger than that of stopper 104 are provided on the outer surface of flexible portion 3. First fixing member 98 is threadably engaged with threaded portion 102 and fixed thereto by fixing ring 110. Second fixing member 100 is threadably engaged with threaded portion 106 and fixed thereto by fixing member 112. As shown in FIG. 9, projecting portions 98A project from first fixing member 98 at 90° intervals in the circumferential direction, and projecting portions 100A project from second fixing member 100 at 90° intervals in the circumferential direction. Projecting portions 98A and 100A oppose each other. Wire 42 of actuator 32 is coupled to projecting portions 98A, and pipe 50 of actuator 32 is coupled to projecting portions 100A. Therefore, four actuators 32 are arranged parallel to each other at equal intervals in the circumferential direction around bending portion 5 of insertion section 2. When a fluid is selectively supplied to actuator 32, actuator 32 is radially expanded and longitudinally contracted. When a fluid is discharged from actuator 32, actuator 32 is radially contracted and longitudinally expanded. Pipe 50 connected to actuator 32 is connected to insertion section 2 through an air-supply tube or air-supply path 62 and is connected to air-supply pump 66 through the interiors of an operation portion and a universal cord (neither of which are shown). A fluid control unit or switching valve 64 is provided at an intermediate portion of path 62 to cause path 62 to communicate with pump 66 or to open it to the outer atmosphere.

An operation of the endoscope according to the second embodiment will be described below.

Normally, as shown in FIG. 7, since an inner space of actuator 32 communicates with the atmosphere, actuator 32 is radially contracted and longitudinally expanded. Therefore, bending portion 5 of insertion section 2 is kept straight. In order to bend bending portion 5 of insertion section 2 upward, a fluid supplied from pump 66 is supplied to one actuator 32 located at an upper portion through path 62. When the fluid is supplied to actuator 32 at the upper portion, actuator 32 is radially expanded and hence is longitudinally contracted as shown in FIG. 8. Therefore, since the length of this actuator is reduced smaller than those of other actuators 32, distal end constitution portion 7 is pulled by actuator 32 located at the upper portion and bending portion 5 is bent upward. That is, by controlling valve 64 to selectively supply the fluid to desired actuator 32, bending portion 5 can be bent to move distal end constitution portion 7 in a desired direction.

Note that in the second embodiment, actuators 32 are provided in bending portion 5 to bend it. However, in an endoscope incorporating a typical wire-type bending mechanism, actuators 32 may be provided in flexible portion 3 to forcibly bend it. Therefore, the insertion portion can be bent stepwise.

Figure 11:
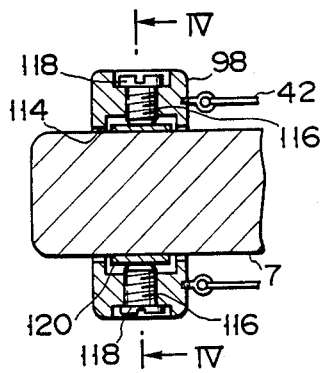
FIG. 11 is a longitudinal sectional view of a first modification of the mounting portion of the elastic actuator according to the second embodiment.
Figure 12:
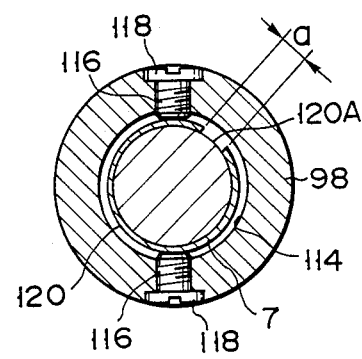
FIG. 12 is a cross-sectional taken along line IV—IV of FIG. 11.

FIGS. 11 and 12 disclose a first modification of the elastic actuator mounting portion according to the second embodiment.

In this modification, elastic actuator 32 is detachably mounted in insertion section 2. That is, first fixing member 98 has fitting hole 114 having a diameter larger than that of distal end constitution portion 7. Two screw holes 116 are formed in first fixing member 98 to oppose each other in the radial direction, and set screw 118 is threadably engaged with each hole 116. Clamping ring 120 consisting of a C-ring-shaped leaf spring is provided inside hole 114 of first fixing member 98. Ring 120 has notch portion 120A partially in the circumferential direction and hence has elasticity in the radial direction. Therefore, when screw 118 is screwed to urge ring 120, a width of notch portion 120A is reduced, and ring 120 clamps distal end constitution portion 7 to fix first fixing member 98. When screw 118 is loosened, a width of notch portion 120A is increased by a recovering force of ring 120, and ring 120 can be detached from distal end constitution portion 7. Note that the second fixing member (not shown) mounted on the front end portion of flexible portion 3 may have a structure similar to that of the first fixing member so that actuator 32 can be attached to/detached from insertion section 2.

FIG. 13 discloses a second modification of the elastic actuator mounting portion. In the second modification, elastic actuator 32 is detachably mounted in insertion section 2 as in the first modification. That is, first magnet 122 is mounted on an outer surface of distal end constitution portion 7, and second magnet 124 is mounted inside fitting hole 126 of first fixing member 98. Therefore, first fixing portion 98 is fixed to distal end constitution portion 7 by a magnetic attractive force. This magnetic attractive force has power larger than that of an extension force in the axial direction which acts when bending portion 5 is bent. Actuator 32 can be detached from insertion section 2 by urging first fixing member 98 in the axial direction by fingers or the like. Note that the second fixing member (not shown) mounted on the front end portion of flexible portion 3 may have a structure similar to that of the first fixing member so that actuator 32 can be attached to/detached from insertion section 2.

FIG. 14 discloses another modification which is basically the same as the second modification. In this modification, wires 42 are connected to both ends of elastic actuator 32, and the other ends of wires 42 are connected to first and second fixing members 98 and 100, respectively, so that actuator 32 is mounted in an insertion portion. Air-supply path 50 is provided outside second fixing member 100 to communicate with actuator 32. Therefore, in this modification, actuator 32 can be mounted at a given position in the circumferential direction of insertion section 2.

Note that since bending portion 5 of insertion section 2 of the endoscope tends to be straight when no load acts thereon, it can be straightened by discharging a fluid in elastic actuator 32. However, the insertion portion may be straightened by supplying the fluid to all actuators 32.

As shown in FIG. 15, when portion to be observed 128 is a cavity which extends horizontally and distal end constitution portion 7 is moved forward along the cavity, bending portion 5 is sometimes bent downward by the weight of distal end constitution portion 7. In this case, by supplying a fluid to upper elastic actuator 32 to expand it, bending portion 5 can be straightened.

A third embodiment of the endoscope according to the present invention will be described below.

Figure 16:
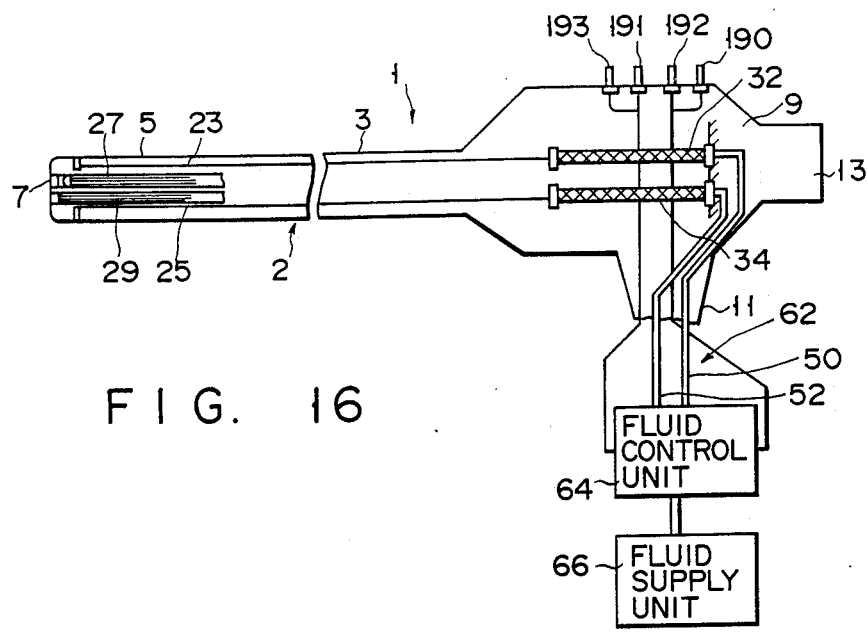
FIGS. 16 and 17 are schematic side views of a third embodiment according to the present invention.
Figure 17:
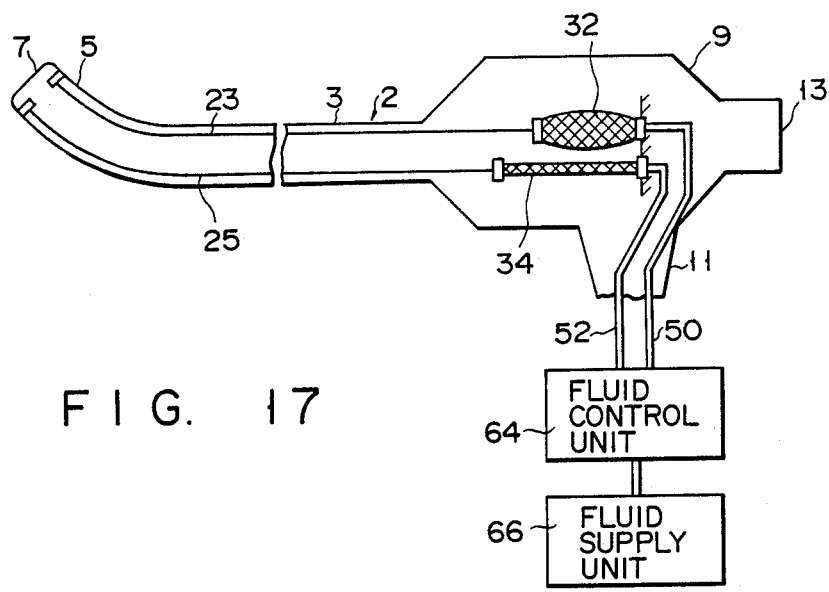
Figure 18:
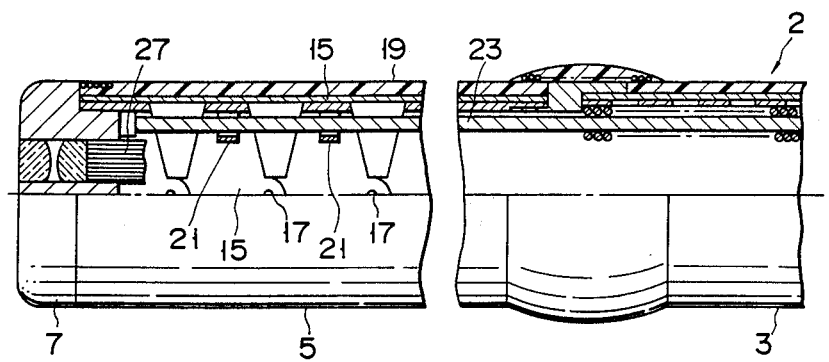
FIG. 18 is a partial sectional view of an insertion portion of the endoscope shown in FIGS. 16 and 17.

Main body 1 of an endoscope shown in FIGS. 16 and 17 has operation section 9, insertion section 2, and universal cord 11. Eyepiece portion 13 is provided to operation section 9, and distal end constitution portion 7 is provided at a distal end portion of insertion section 2. Insertion section 2 has flexible portion 3 and bending portion 5, and distal end constitution portion 7 is provided at the distal end of bending portion 5. As shown in FIG. 18, bending portion 5 is constituted by pivotally coupling a plurality of bend tops 15 by pins 17 and covering the coupled tops and pins by cover 19. Wire guide 21 is provided on an inner surface of each top 15, and angle wire 23 is inserted through guide 21. Distal end portions of wires 23 and 25 are coupled to distal end constitution portion 7, and proximal end portions extend to operation section 9 through insertion section 2. Observation optical system 27, illumination optical system 29, and the like each consisting of an optical fiber bundle are arranged together with wires 23 and 25 in insertion section 2.

Figure 19:
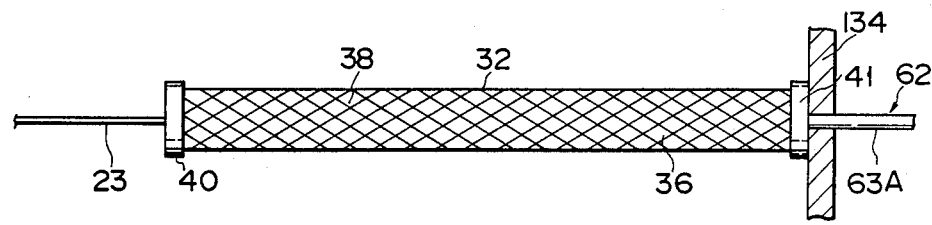
FIG. 19 is a side view of an elastic actuator.

As shown in FIGS. 16, 17, and 19, elastic actuators 32 and 34 are housed parallel to each other in operation section 9. Each of actuators 32 and 34 has synthetic rubber tube 36 therein. Tube 36 is covered with meshlike tube 38, and mouthpieces 40 and 41 are coupled to both ends of tube 36. Air-supply path 62 which communicates with an inner space of tube 36 is connected to mouthpiece 41, and the other ends of wires 23 and 25 are connected to mouthpiece 40. That is, wire 23 is connected to actuator 32, and wire 25 is connected to actuator 34. Mouthpiece 41 of each of actuators 32 and 34 having the above arrangement is fixed to base 134 of operation section 9 so that each actuator is held by main body 1 of the endoscope. Path 62 consists of air-supply tubes 50 and 52 which communicate with a fluid supply unit or air-supply pump 66 through a fluid control unit or switching valve 64. Actuators 32 and 34 are longitudinally expanded/contracted by a pressure of a fluid supplied therein. That is, when the fluid is supplied to actuators 32 and 34, they are radially expanded and hence longitudinally contracted. When the fluid is discharged from actuators 32 and 34, they are radially contracted and longitudinally expanded.

Figure 20:
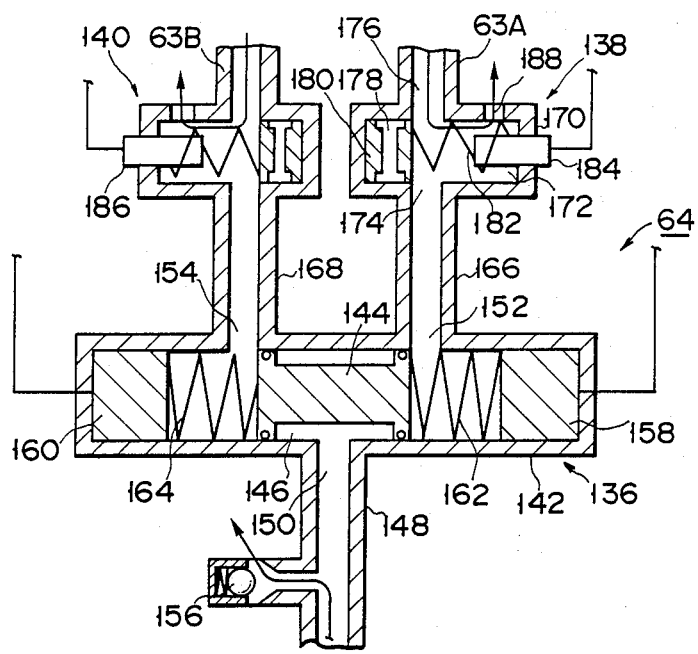
FIGS. 20 and 21 are longitudinal sectional views of a fluid control unit according to the third embodiment of the present invention.
Figure 21:
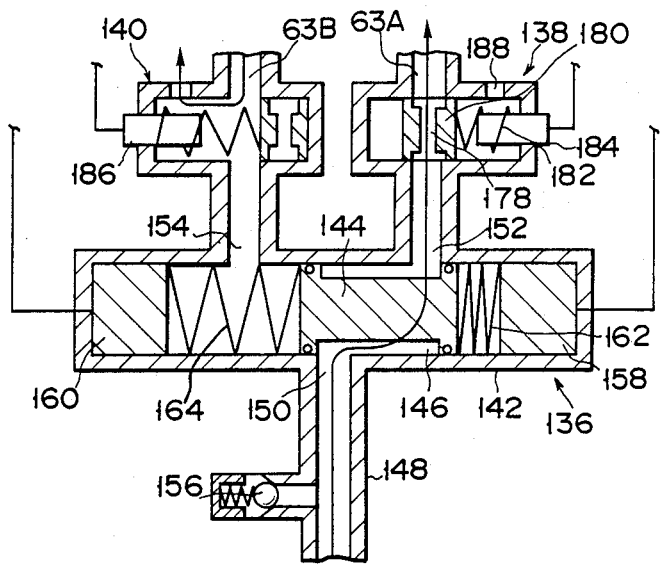

Valve 64 as the fluid control unit is constituted as shown in FIGS. 20 and 21. That is, valve 64 includes main valve 136, first auxiliary valve 138, and second auxiliary valve 140. First, main valve 136 will be described below. Main valve 136 has valve main body 142, and valve chamber 146 which houses spool valve 144 to be slidable in a left-to-right direction is provided in valve main body 142. First port 150 which communicates with pump 66 through pipe 148 is provided in a central portion of valve main body 142. Second and third ports 152 and 154 are provided at upper left and right portions of first port 150. Note that ball valve 156 is provided at an intermediate portion of communication pipe 148 so that pipe 48 communicates with the atmosphere. First and second electromagnets 158 and 160 are provided at both end portions of chamber 146. Compression springs 162 and 164 are provided between both end faces of spool valve 144 and electromagnets 158 and 160 and maintain spool valve 144 in a neutral state. Second port 152 is connected to first auxiliary valve 138 through communication pipe 166, and third port 154 is connected to second auxiliary valve 140 through communication pipe 168. Since first and second auxiliary valves 138 and 140 have the same structure, only first auxiliary valve 138 will be described. Valve 138 has valve main body 170, and valve chamber 172 is formed in valve 138. Fourth and fifth ports 174 and 176 are formed to oppose each other in the side walls of valve main body 170. Fourth port 174 is connected to main valve 136 through pipe 166, and fifth port 176 is connected to elastic actuator 32 through tube 50, respectively. Valve member 180 having through port 178 is movably housed in chamber 172 and biased to the left by compression spring 182. Third electromagnet 184 is provided to the right of valve main body 170 (fourth electromagnet 186 is provided to second auxiliary valve 140), and leak port 188 which communicates with chamber 172 is provided in valve main body 170. First to fourth electromagnets 158, 160, 184, and 186 are electrically connected to first to fourth switches 190 to 193 provided in operation portion 193.

An operation of the endoscope having the above arrangement will be described below. Normally, first to fourth switches 190 to 193 are kept off, and electromagnets 158, 160, 184, and 186 of main valve 136 and first and second auxiliary valves 138 and 140 are deenergized. Therefore, first port 150 of main valve 136 is closed by spool valve 144, and a fluid supplied from pump 66 leaks from ball valve 156 into the atmosphere. At the same time, valve members 180 of first and second auxiliary valves 138 and 140 are biased by springs 182, and fifth port 176 communicates with leak port 188. As a result, actuators 32 and 34 communicate with the atmosphere through tubes 50 and 52 and are kept longitudinally expanded. Wires 23 and 25 are pushed to keep bending portion 5 of insertion section 2 straight.

Then, if, for example, first switch 190 is turned on, first electromagnet 158 is energized, and spool valve 144 is attracted to the right against a biasing force of spring 162. Therefore, first and second ports 150 and 152 of main valve 136 communicate with each other through a recess of spool valve 144. At the same time, third electromagnet 184 of first auxiliary valve 138 is energized, and therefore fourth and fifth ports 174 and 176 communicate with each other via through port 178 of valve member 180. As a result, a fluid supplied from pump 66 is supplied to actuator 32 through switching valve 64 and tube 50, and actuator 32 is radially expanded and hence longitudinally contracted. Therefore, wire 23 coupled to actuator 32 is extended, and bending portion 5 of insertion section 2 is bent upward as shown in FIG. 17.

In the endoscope according to this embodiment, first to fourth switches 190 to 193 are selectively operated to energize or deenergize electromagnets 158, 160, 184, and 186 of switching valve 64. As a result, actuators 32 and 34 are pushed or pulled to bend bending portion 5 in a desired direction.

Figure 22:
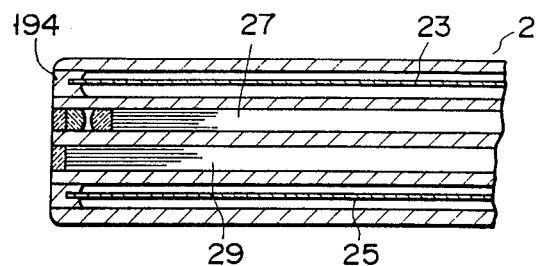
FIG. 22 is a longitudinal sectional view of a modification of the insertion portion of the endoscope according to the third embodiment.

Note that in the third embodiment, a bending operation of the insertion portion having a plurality of bend tops in the bending portion is described. However, even in an endoscope having a small diameter without bend tops as shown in FIG. 22, a bending operation can be performed by coupling the distal ends of wires 23 and 25 to wire fixing member 194 provided at the distal end of insertion section 2.

Figure 23:
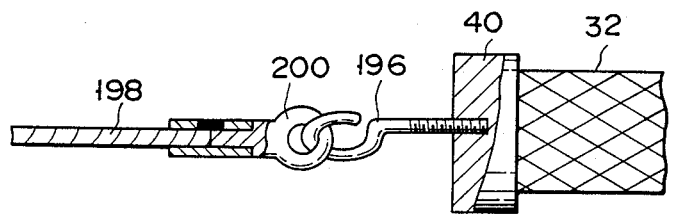
FIGS. 23 and 24 are partially cutaway side and plan views of modifications of the elastic actuator, respectively.
Figure 24:
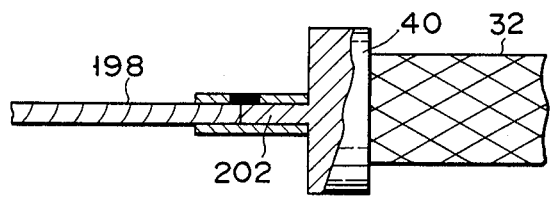

The elastic actuator may be coupled to the angle wire in the manner to be described below. That is, as shown in FIG. 23, anchor bolt 196 is screwed into mouthpiece 40, and coupling metal piece 200 is brazed to angle wire 198, thereby engaging metal piece 200 with bolt 196. Moreover, as shown in FIG. 24, projecting pin 202 may be provided to mouthpiece 40 and brazed to wire 198.

Figure 25:
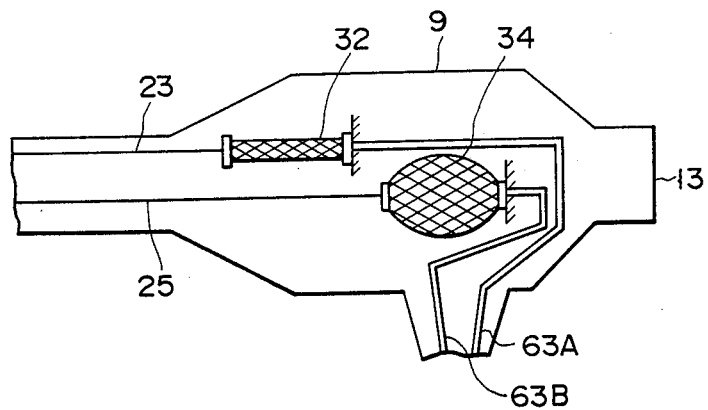
FIG. 25 is a schematic side view of a modification of the elastic actuator according to the third embodiment.
Figure 34:
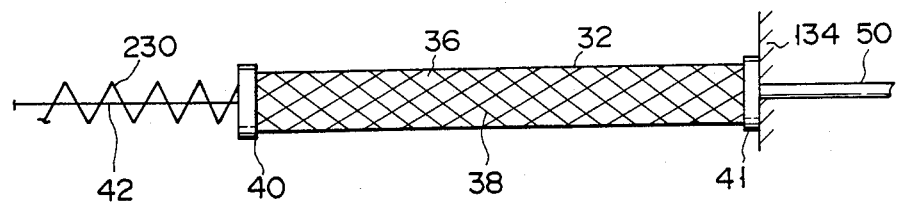
FIGS. 34 and 35 are side views of an elastic actuator according to the fourth embodiment.
Figure 35:
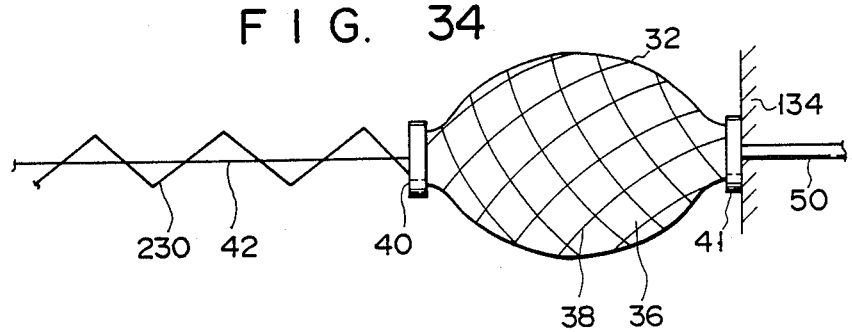

In the third embodiment, two actuators are parallelly arranged in the insertion portion of the endoscope. However, as shown in FIG. 25, actuators 32 and 34 may be arranged offset from each other in the longitudinal direction. In this case, when actuator 34 is expanded as shown in FIG. 25, it is not brought into contact with or urges actuator 32.

In the third embodiment, the elastic actuators are arranged inside the operation portion. However, as shown in FIGS. 26 to 31, the elastic actuators may be arranged in the insertion portion of the endoscope. That is, insertion section 2 of the endoscope is constituted by coupling proximal-end-side insertion portion 4B and distal-end-side insertion portion 4C each consisting of a tubular member through bending mechanism 6. Pulley 28 is provided in mechanism 28, and an intermediate portion of angle wire 42 is wound around pulley 28. Elastic actuators 32 and 34 are housed offset from each other in the longitudinal direction in proximal-end-side insertion portion 4B, and an end portion of wire 42 is coupled to mouthpiece 40 of each of actuators 32 and 34. Air-supply tubes 50 and 52 are connected to actuators 32 and 34 so that a fluid is supplied to or discharged from the actuators. Therefore, when the fluid is selectively supplied to or discharged from actuators 32 and 34, distal-end-side insertion portion 4C can be bent about mechanism 6.

A fourth embodiment of the endoscope according to the present invention will be described below with reference to FIGS. 32 to 36. As shown in FIG. 32, main body 1 of an endoscope has operation section 9, insertion section 2, and universal cord 11. Eyepiece portion 13 is provided to operation section 9, and distal end constitution portion 7 is provided to a distal end portion of insertion section 2. Housing 7A of distal end constitution portion 7 is formed of a metal or synthetic resin material and is covered with cover 19 formed of an insulating material such as rubber or a synthetic resin material. Space 212 defined by circumferential wall 206, front wall 208, and rear wall 210 is formed in housing 7A. Side-viewing observation window 214 is formed in circumferential wall 206, and direct-viewing observation window 216 is formed in front wall 208. Optical fiber bundle 218, objective lens 220, and protection tube 222 for covering bundle 218 and lens 20 are provided to rear wall 210 of housing 7A, and lens 220 opposes direct-viewing observation window 216. Bundle 218, lens 220, and reflecting mirror 224 constitute observation optical system 27. That is, mirror 224 is arranged in space 21 of housing 7A such that its reflecting surface 224A faces upward and its one end is pivotally mounted on hinge pin 226 mounted between windows 214 and 216 in housing 7A. On end of wire 42 is connected to the other end portion, i.e., a free end of mirror 224, and the other end of wire 42 is connected to elastic actuator 32 via a through hole of rear wall 210. Wire 42 is guided by guide roller 228.

Elastic actuator 32 will be described below. Actuator 32 has synthetic rubber tube 36 therein. Tube 36 is covered with mesh-like tube 38, and mouthpieces 40 and 41 are coupled to both end portions of tube 36. Air-supply tube 50 or air-supply path 62 which communicates with an interior of tube 36 is connected to mouthpiece 41, and the other end of wire 42 is connected to mouthpiece 40. Actuator 32 having the above arrangement is provided behind rear wall 210 of housing 7A in insertion section 2 and held therein by fixing mouthpiece 41 to support member 134. Tension spring 230 is mounted between mouthpiece 40 and rear wall 210. Actuator 32 is longitudinally expanded/contracted by a pressure of a fluid supplied to its inner space. That is, when the fluid is supplied to actuator 32, actuator 32 is radially expanded and hence longitudinally contracted. When the fluid is discharged from actuator 32, actuator 32 is radially contracted and hence longitudinally expanded.

Air-supply tube 50 connected to actuator 32 is guided to light source unit 232 through the interiors of insertion section 2 and universal cord 11 and is connected to air-supply pump 66 as a fluid supply unit through solenoid 64 as a fluid control unit. Solenoid 64 is electrically connected to switch 236 provided in operation section 9 through signal line 234 which is inserted in cord 11.

Figure 36:
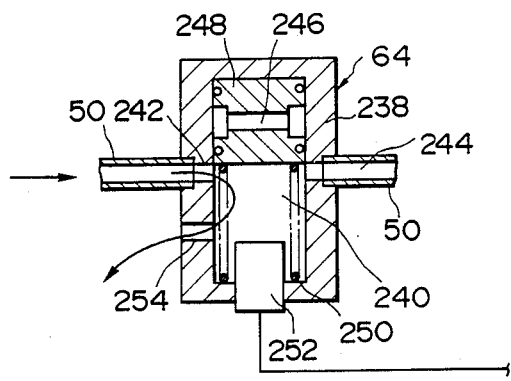
FIG. 36 is a longitudinal sectional view of a fluid control unit according to the fourth embodiment.

Solenoid 64 is constituted as shown in FIG. 36. That is, valve chamber 240 is provided in valve main body 238, and first and second ports 242 and 244 are formed to oppose each other in side walls which define chamber 240. First port 242 is connected to pump 66 through tube 50, and second port 244 is connected to actuator 32 through tube 50, respectively. Valve member 248 having through port 246 is housed to be vertically movable in chamber 240 and is biased upward by compression spring 250. Solenoid 252 is provided at a lower portion of valve main body 238 to oppose a lower surface of valve member 248. Leak port 254 is provided in the side wall and communicates with chamber 240.

In solenoid 64, when switch 236 is turned on to energize electromagnet 252, valve member 248 is attracted against a biasing force of spring 250, so that first and second ports 242 and 244 communicate with each other via through port 246 of valve member 248. When switch 236 is turned off to deenergize electromagnet 252, valve member 248 is moved upward by the biasing force of spring 250, so that first and second ports 242 and 244 communicate with leak port 254. Therefore, by turning on or off switch 236 to energize or deenergize solenoid 64, tube 50 communicates with pump 66 or the atmosphere.

An operation of the endoscope according to the fourth embodiment will be described below.

Normally, switch 236 is kept off, so that electromagnet 252 of solenoid 64 is deenergized. Therefore, valve member 248 is moved upward by the biasing force of spring 250, and first and second ports 242 and 244 communicate with leak port 254. As a result, a fluid supplied from pump 66 leaks into the atmosphere through leak port 254. At the same time, elastic actuator 32 communicates with the atmosphere through tube 5 and hence is longitudinally expanded by an extension force of spring 230. Wire 42 is moved forward by expansion of actuator 32, and mirror 224 is set at an inclination angle of 45°. In this state, a body cavity is observed through side-viewing observation window 214. That is, the endoscope according to the fourth embodiment is used as a side-viewing endoscope. When switch 32 is turned on, electromagnet 252 of solenoid 64 is energized, and valve member 248 is attracted against the biasing force of spring 250. Therefore, first and second ports 242 and 244 communicate with each other via through port 246 of valve member 248 to close leak port 254. As a result, a fluid supplied from pump 66 is supplied to actuator 32 through tube 50. When the fluid is supplied to actuator 32, actuator 32 is radially expanded and hence longitudinally contracted. For this reason, wire 42 is moved backward against the biasing force of spring 230, and mirror 224 is pivoted about pin 226 in a direction indicated by an arrow in FIG. 33. As a result, mirror 224 is moved outside an optical path between direct-viewing observation window 216 and lens 220. In this state, a body cavity is observed through window 216, i.e., this endoscope is used as a direct-viewing endoscope.

As described above, in the endoscope according to the fourth embodiment, by turning on or off switch 236, a fluid is supplied to or discharged from elastic actuator 32, and therefore actuator 32 is longitudinally expanded or contracted. As a result, mirror 224 is pivoted to change an observation field.

FIG. 37 discloses a modification of the endoscope according to the fourth embodiment. In this modification, focus adjustment of an observation optical system can be performed by elastic actuator 32. That is, observation window 256 and guide hole 258 are provided in housing 7A of distal end constitution portion 7. Lens frame 260 which holds objective lens 220 is arranged in hole 258 to be movable along the optical axis. Projecting piece 262 is provided to lens frame 260, and operation wire 42 connected to actuator 32 is mounted on projecting piece 262. In this modification, actuator 32 is operated as in the fourth embodiment, and frame 260 is moved forward/backward along the optical axis through wire 42, thereby adjusting a focal point of lens 220.

FIGS. 38 and 39 disclose still another modification of the endoscope. In this modification, elastic actuator 32 is provided in operation section 9 of the endoscope to change an observation field or to perform focus adjustment of an objective lens. That is, mouthpiece 41 of actuator 32 is fixed to main body 264 of operation section 9, and operation wire 42 is connected to mouthpiece 40. Wire 42 is connected from operation portion main body 264 to a driven portion through insertion section 2. Therefore, the driven portion can be driven by a forward/backward movement of wire 42.

Note that since elastic actuator 32 in the above embodiments is formed of rubber tube 36, it has elasticity in radial and axial directions and hence can recover an original shape by itself. Therefore, when tube 36 communicates with the atmosphere, a fluid in tube 36 can be discharged by a recovering force of tube 36. That is, tension spring 230 need not be provided.

A fluid is not limited to a gas but may be a liquid such as water or oil.

What is claimed is:

1. An endoscope comprising:
    a flexible insertion section having distal and proximal end portions;
    elastic actuators mounted in said insertion section, each one of said elastic actuators having an inner space and fluid-supply means for supplying/discharging a fluid to/from said inner space and being longitudinally expanded/contracted when the fluid is supplied to/discharged from said inner space;
    converting means for converting the expansion/contraction of each said elastic actuator into a bending motion of said insertion section; and
    control means for controlling the supply/discharge of the fluid of said fluid-supply means to said inner space of each said elastic actuator,
    each said elastic actuator comprising a synthetic rubber tube for defining said inner space and a mesh-like tube covering an outer surface of said synthetic rubber tube for allowing only radial expansion of the latter, whereby the latter longitudinally contracts, and
    each said fluid-supply means comprising mouthpieces respectively mounted on opposite end portions of said synthetic rubber tube of each said elastic actuator.

2. An endoscope according to claim 1, wherein said elastic actuator comprises:
    a synthetic rubber tube, a plurality of wire members being embedded in a circumferential wall of said synthetic rubber tube to be parallel to each other at predetermined intervals in a longitudinal direction;
    a mesh-like tube for covering an outer surface of said synthetic rubber tube; and
    mouthpieces mounted on both end portions of said synthetic rubber tube.

3. An endoscope according to claim 1, wherein said insertion portion comprises a plurality of segments sequentially coupled with each other through joint portions.

4. An endoscope according to claim 3, wherein said converting means comprises a pulley mounted on an end portion of each of said segments and a wire, one end of which is connected to the end portion of said elastic actuator, and the other end of which is connected to said pulley.

5. An endoscope according to claim 1, wherein said elastic actuator is arranged on an outer surface of said insertion section to be parallel to an axial direction of said insertion section.

6. An endoscope according to claim 5, wherein said elastic actuator is detachably mounted on said insertion section by joint members.

7. An endoscope according to claim 1, further comprising:
    an operation section, provided in the proximal end portion of said insertion section, for adjusting a bent angle of said insertion section; and
    an operation wire for bending said insertion section, said operation wire being inserted in said insertion section, and the distal end of said wire being fixed to the distal end portion of said insertion section, and wherein
    one end of said elastic actuator is fixed to a main body of said operation section, and the other end thereof is connected to the proximal end of said operation wire.

8. An endoscope according to claim 1, wherein said fluid control means comprises a pump for supplying the fluid to said elastic actuator, fluid conducting means which communicates with said pump and said elastic actuator, and valve means for opening/closing or switching said fluid conducting means.

9. An endoscope according to claim 1, further comprising:
    an observation optical system provided in the distal end portion of said insertion section, said observation optical system having a driven portion; and
    a second elastic actuator for driving said driven portion of said observation optical system.

10. An endoscope according to claim 9, wherein said driven portion of said observation optical system comprises a reflecting mirror pivotally mounted to change an observation field of said endoscope and driven by said second elastic actuator.

11. An endoscope according to claim 9, wherein said driven portion of said observation optical system comprises a focus adjusting mechanism driven by said second elastic actuator.

12. An endoscope comprising:
    an insertion section having distal and proximal end portions;
    an observation optical system in said distal end portion and having a driven portion;
    an elastic actuator for driving said driven portion of said observation optical system, said elastic actuator having an inner space and fluid-supply means for supplying/discharging a fluid to/from said inner space means and being longitudinally expanded/contracted when the fluid is supplied to/discharged from said inner space; and
    control means for controlling the supply/discharge of the fluid of said fluid-supply means to said inner space of said elastic actuator.
    said elastic actuator comprising a synthetic rubber tube for defining said inner space and a mesh-like tube covering an outer surface of said synthetic rubber tube for allowing only radial expansion of the latter, whereby the latter longitudinally contracts, and
    said fluid-supply means comprising mouthpieces mounted on opposite end portions of said synthetic rubber tube.

13. An endoscope according to claim 12, wherein said electric actuator comprises:
    a synthetic rubber tube, a plurality of wire members being embedded in a circumferential wall of said synthetic rubber tube to be parallel to each other at predetermined intervals in a longitudinal direction;
    a mesh-like tube for covering an outer surface of said synthetic rubber tube; and
    mouthpieces mounted on both end portions of said synthetic rubber tube.

14. An endoscope according to claim 12, further comprising:
    an operation wire for driving said observation optical system, the distal end of said operation wire being connected to said driven portion of said observation optical system, and the proximal end thereof being connected to said elastic actuator.

15. An endoscope according to claim 12, wherein said fluid control means comprises a pump for supplying the fluid to said elastic actuator, fluid conducting means which communicates with said pump and said elastic actuator, and valve means for opening/closing or switching said fluid conducting means.

16. An endoscope according to claim 12, wherein said driven portion of said observation optical system comprises a reflecting mirror pivotally mounted to change an observation field of said endoscope and driven by said elastic actuator.

17. An endoscope according to claim 12, wherein said driven portion of said observation optical system comprises a focus adjusting mechanism driven by said actuator.

18. An endoscope according to claim 3, wherein said converting means comprises a pulley mounted on an end portion of said distal end portion, and a wire, one end of which is connected to an end portion of said elastic actuator, and the other end of which is connected to said pulley.

19. An endoscope according to claim 1, wherein said elastic actuator is detachably mounted on said insertion section by joint members.

* * * * *